US011083988B2

(12) United States Patent
Oltmanns

(10) Patent No.: US 11,083,988 B2
(45) Date of Patent: Aug. 10, 2021

(54) SCENTED FURNACE FILTER

(71) Applicant: Derick Rudy Oltmanns, Lake Country (CA)

(72) Inventor: Derick Rudy Oltmanns, Lake Country (CA)

( * ) Notice: Subject to any disclaimer, the term of this patent is extended or adjusted under 35 U.S.C. 154(b) by 176 days.

(21) Appl. No.: 16/547,649

(22) Filed: Aug. 22, 2019

(65) Prior Publication Data
US 2021/0053003 A1 Feb. 25, 2021

(51) Int. Cl.
*B01D 46/00* (2006.01)
*A61L 9/12* (2006.01)
*B01F 3/04* (2006.01)

(52) U.S. Cl.
CPC ........... *B01D 46/0038* (2013.01); *A61L 9/12* (2013.01); *A61L 9/127* (2013.01); *B01F 3/04* (2013.01); *A61L 2209/133* (2013.01); *B01D 2279/50* (2013.01)

(58) Field of Classification Search
CPC ....... B01D 46/0038; A61L 9/12; A61L 9/127; B01F 3/04
See application file for complete search history.

(56) References Cited

U.S. PATENT DOCUMENTS

2011/0243788 A1* 10/2011 Garten .................... A61L 9/122
422/4

* cited by examiner

*Primary Examiner* — Robert A Hopkins
(74) *Attorney, Agent, or Firm* — Capeheart Law Firm

(57) ABSTRACT

A scented furnace filter that allows to evaporate scented liquid to create scent at supply registers. The scented furnace filter having a filter frame installed in a furnace coupled with a filter material. The filter frame having a permeable filter frame top section. A scented liquid bar containing a scented liquid and having a permeable scented liquid bar base is coupled to an activation tab. The scented liquid bar is coupled to the permeable filter frame top section. When the activation tab is moved, either partially or completely, the scented liquid permeates through the permeable scented liquid bar base and the permeable filter frame top section to soak the filter material such that air generated by the furnace going through the filter material evaporates the scented liquid to generate scented air to be distributed in a duct system to one or more supply register.

8 Claims, 6 Drawing Sheets

SCENTED FURNACE FILTER

REFERENCE TO PENDING APPLICATIONS

This application does not claim the benefit of pending application.

BACKGROUND OF THE INVENTION

1. Field of the Invention

The present invention in generally directed to a furnace filters, and, more particularly, relates to a scented furnace filter.

2. Description of the Related Art

There are several products used to freshen the air in a room, such as diffusers, wall plug scented oil heater, incense, scented water heaters etc.

These products are costly and have very low scent diffusion radius (e.g. they only freshen the air of a small area like one room). The products are generally not recyclable or reusable.

There is a need for a cost-effective air freshening system that can cover a large surface for a prolonged period of time.

BRIEF SUMMARY

In an aspect of the present invention, a scented furnace filter is disclosed. The scented furnace filter includes a filter frame installed in a furnace coupled with a filter material and having a permeable filter frame top section. A scented liquid bar coupled to the permeable filter frame top section. The scented liquid bar containing a scented liquid and having a permeable scented liquid bar base coupled to a removable activation tab acting as a waterproof barrier to prevent the scented liquid from leaking, wherein when the activation tab is removed, the scented liquid permeates through the permeable scented liquid bar base and the permeable filter frame top section to soak said filter material such that air generated by the furnace going through the filter material evaporates the scented liquid to generate scented air to be distributed in a duct system.

The features of the invention which are believed to be novel are particularly pointed out in the specification. The present invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
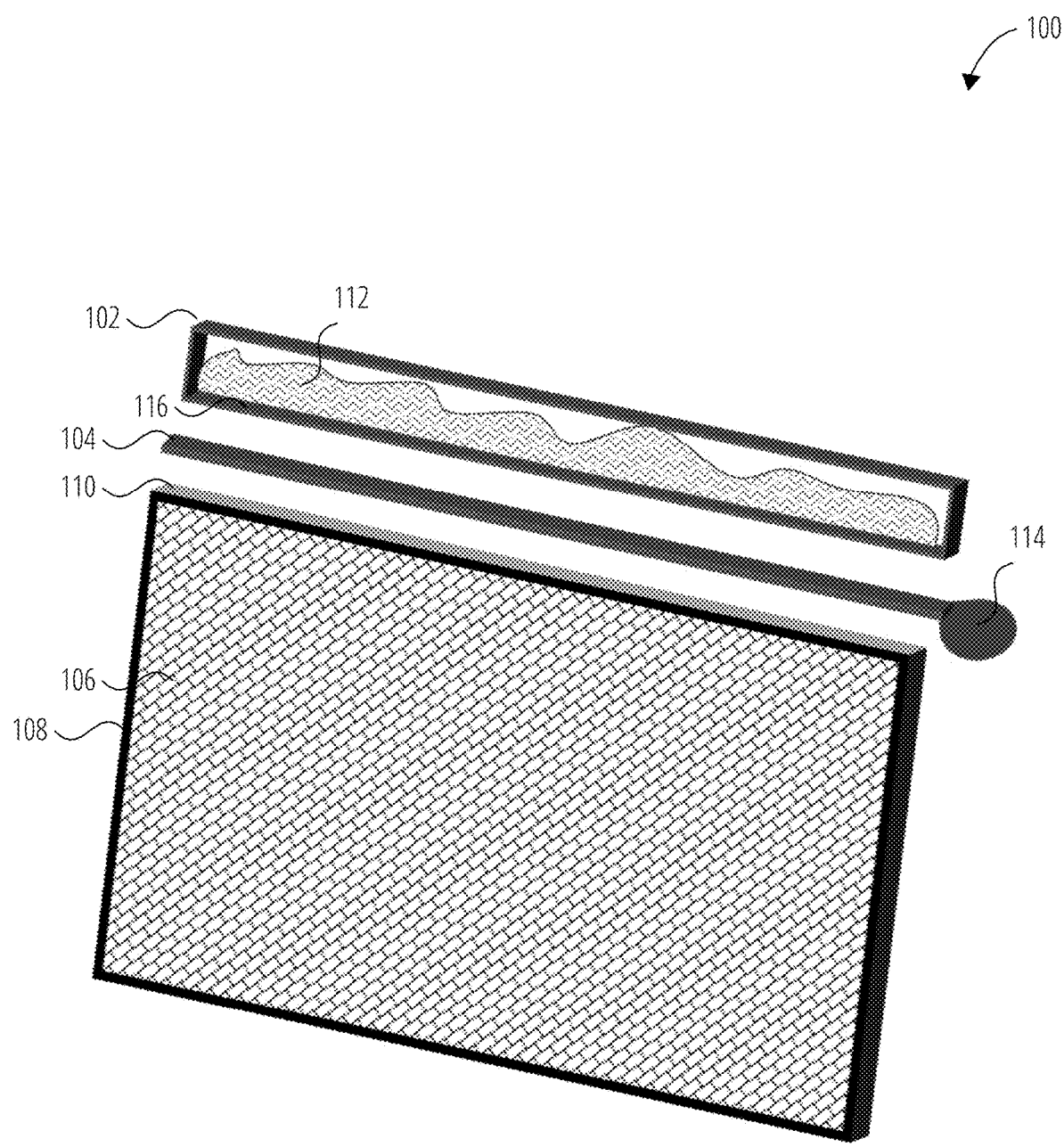
FIG. 1 illustrates scented furnace filter components in accordance with one embodiment.

As illustrated in FIG. 1, an embodiment of a scented furnace filter of the present invention is disclosed. This embodiment depicts a scented furnace filter 100. The filter has a filter frame 108 to hold filter material 106. The filter frame 108 is made of substantially solid waterproof material.

The filter material 106 can be made of any known odorless fibers such as fiberglass, polyester, cotton. The filter material 106 can also be made of hemp. The filter material 106 can also be composed of a combination of fibers and/or hemp. Preferably the filter material 106 has spongeous-like characteristics to maintain the moisture from the scented liquid.

In one embodiment, the filter frame 108 can be reused to install replacement filter material 106. The filter frame top section 110 includes permeable material. A scented liquid bar 102 liquid bar is coupled to the filter frame 108. The scented liquid bar 102 is of substantially the same length and depth as the filter frame 108.

At manufacture, the scented liquid bar 102 has five leak proof surfaces. The scented liquid bar base 116 is made of permeable material and at manufacture is covered with a waterproof activation tab 104. The waterproof activation tab 104 is coupled using a pressure sensitive adhesive such that it can be removed by a horizontal force applied on the activation handle 114 which is extruding from the scented furnace filter 100.

The scented liquid bar 102 is filled with a scented liquid 112 and the activation tab 104 creates a waterproof barrier to prevent the scented liquid 112 from leaking before usage.

The scented liquid 112 can be of any known type of liquid which emits a scent during evaporation, such as but not limited to, essential oils. Example of different smells that can be offered include, but not limited to, lavender, apple cinnamon, eucalyptus, vanilla, pine or a combination of different scents.

At manufacture, the scented liquid bar 102 is coupled to the filter frame top section 110. The total dimension of the scented furnace filter 100 (including the filter frame 108 and the scented liquid bar 102) is design to comply to known furnace filter standard size. The coupling between the scented liquid bar 102 and the filter frame top section 110 can be done using clamps, brackets, glue or any other means of securing the two together, such that the activation tab 104 on the scented liquid bar 102 can be outwardly pulled without affecting the coupling of the scented liquid bar 102 and the filter frame 108.

In another embodiment, the scented liquid bar 102 is removable and a refill scented liquid bar 102 can be installed on an existing filter frame 108.

In another embodiment the scented liquid bar 102 can be refilled with scented liquid 112.

Figure 2:
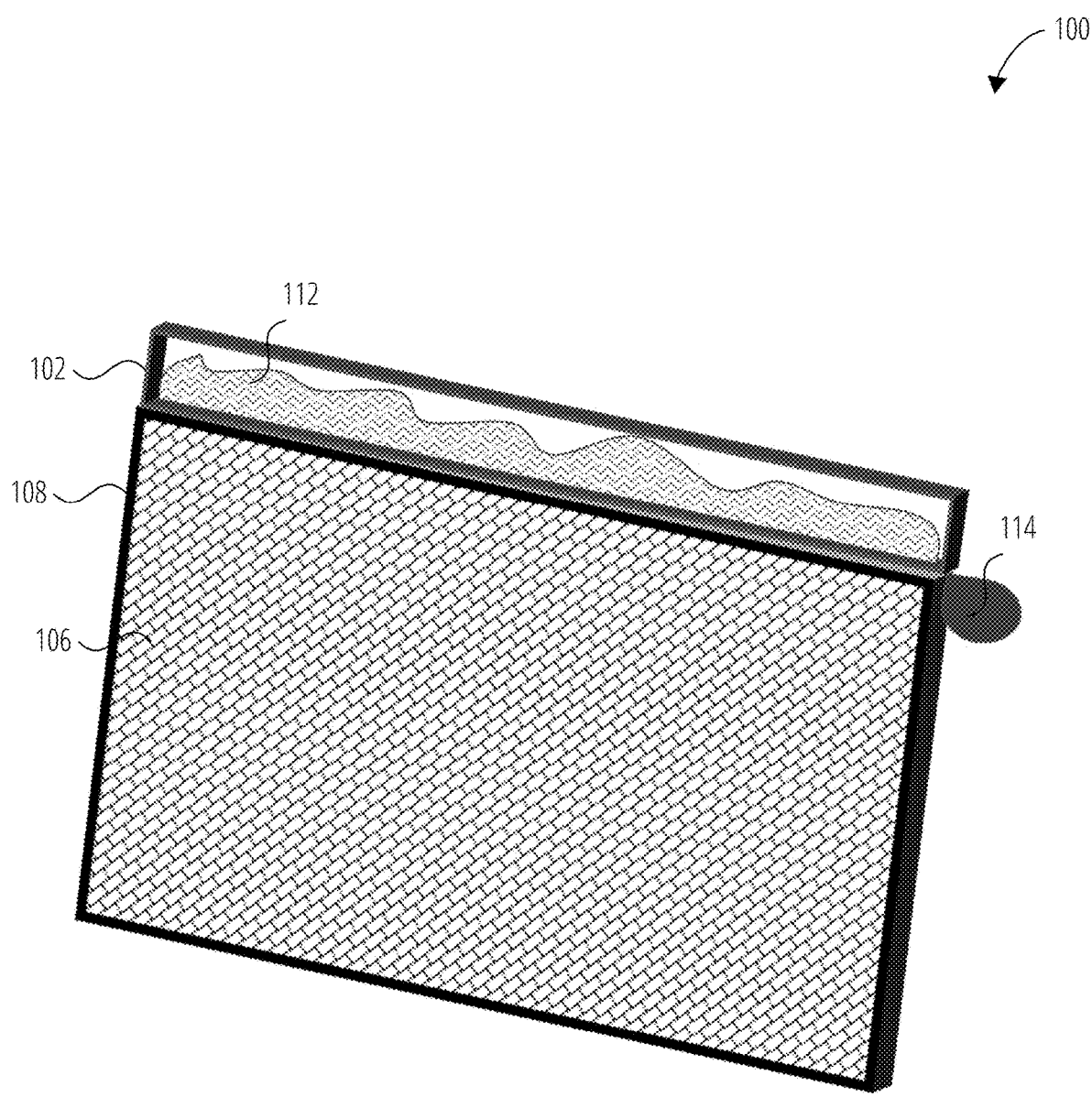
FIG. 2 illustrates the assembled scented furnace filter in accordance with one embodiment.

FIG. 2 depicts the assembled scented furnace filter 100 with the scented liquid bar 102 coupled with the filter frame 108 with the activation tab 104 (not shown) in between the two parts to prevent the scented liquid 112 from leaking.

Figure 3:
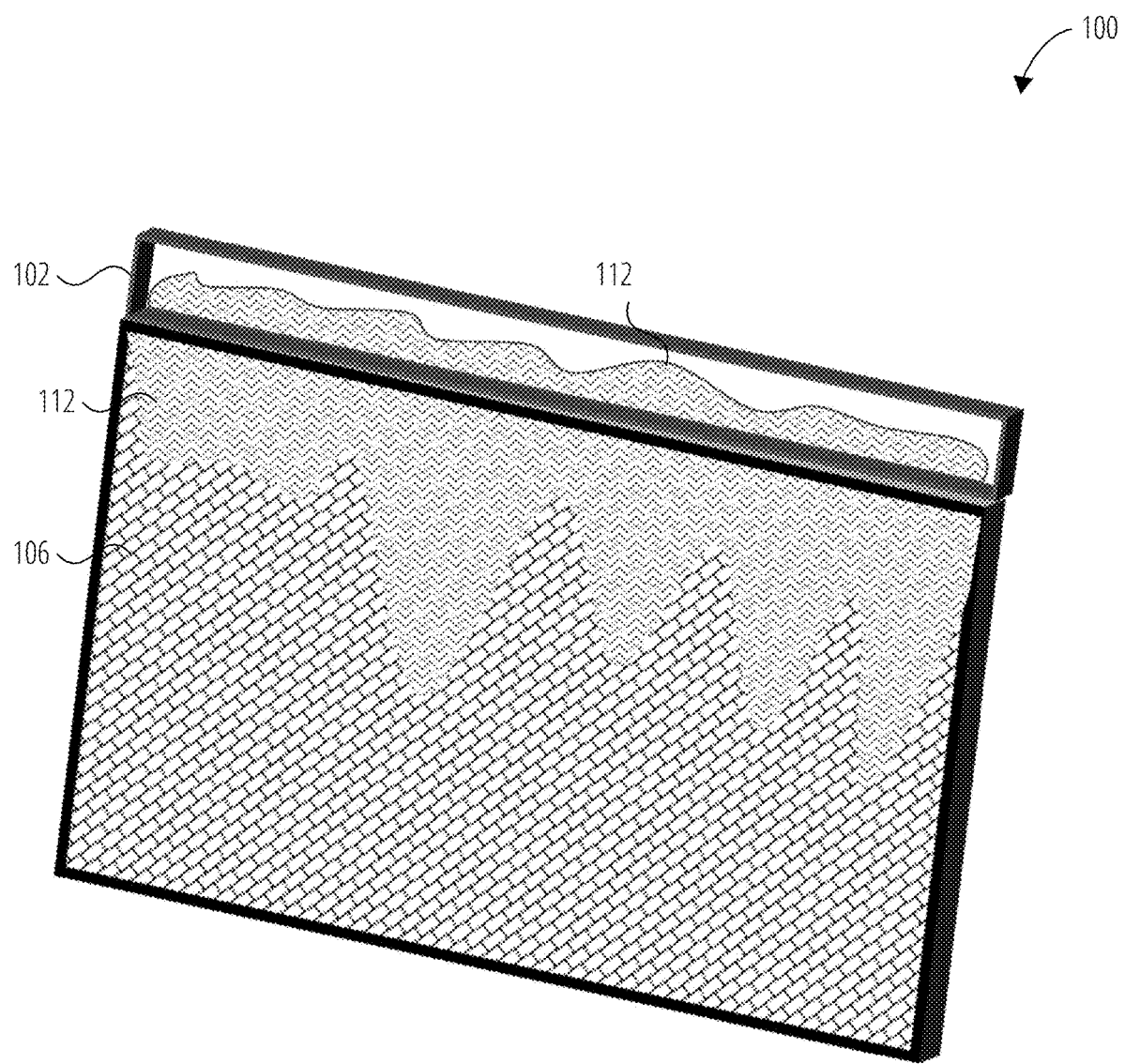
FIG. 3 illustrates an activated scented furnace filter in accordance with one embodiment.

FIG. 3 illustrates an activated scented furnace filter 100. When the scented furnace filter 100 is inserted in the furnace. the scented liquid bar 102 is located at the top. When the activation handle 114 is pulled, the activation tab 104 is slid out from between the scented furnace filter 100 and scented liquid bar 102. With gravity, the scented liquid 112 permeates through the scented liquid bar base 116 and the filter frame top section 110 to soak the filter material 106. The air generated by the furnace and flowing through the filter evaporates the scented liquid 112 to create a scent that is carried through the ducting system to one or more supply registers coupled with the furnace.

Variations in the speed of the furnace air flow will cause more evaporation therefore more scent to be carried through the ducting system. Similarly, if the air being circulated to the furnace is warmer, more evaporation will occur, and more scent will be carried through the duct system.

Figure 4:
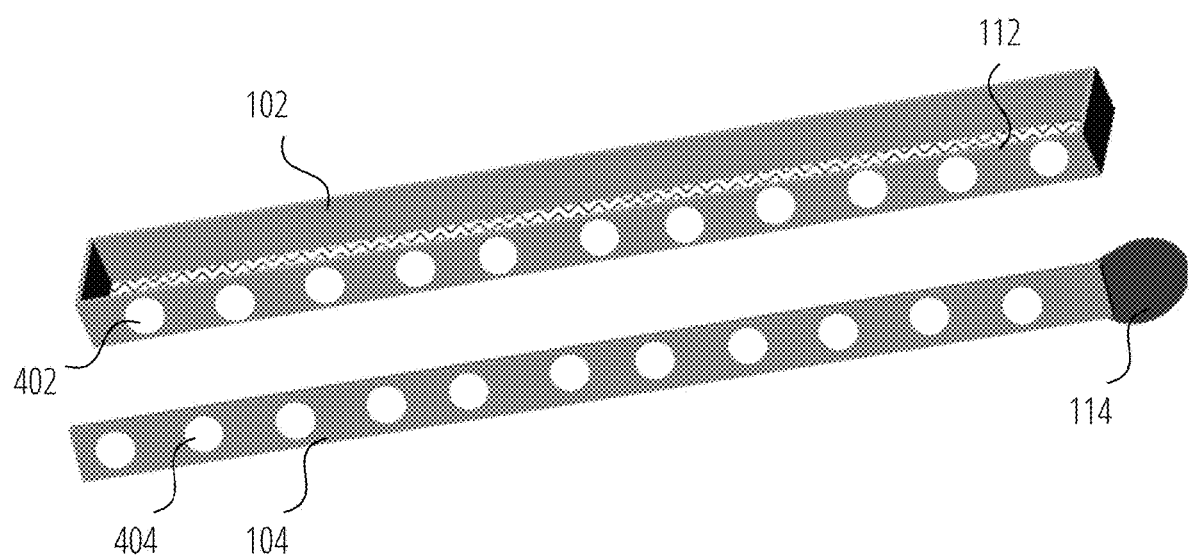
FIG. 4 illustrates a variable liquid distribution activation tab in accordance with one embodiment.

FIG. 4 depicts another embodiment where the amount of scented liquid 112 dripping down to the filter material 106 can be adjusted. In this embodiment, the activation tab 104 is made of substantially rigid material, such as for example plastic. The activation tab 104 comprises one or more activation tab holes 404. The scented liquid bar base 116 is made of waterproof material, except for one or more permeable holes 402. The activation tab holes 404 and the permeable holes 402 are located such that when the activation tab 104 is fully inserted between the scented liquid bar 102 and the filter frame 108, the holes do not overlap creating a waterproof barrier.

When the activation handle 114 is pulled to move the activation tab 104 outwardly from the filter frame 108, the permeable holes 402 and activation tab holes 404 start to overlap allowing some amount of scented liquid 112 to drop through to reach the filter material 106. The size and number of holes can allow more or less liquid to permeate through. The holes can be shaped as ovals or other shape to effect the amount of scented liquid permeating through.

Optionally, the activation tab 104 may have markings to show how much scented liquid is dripping based on the position of the activation tab. In this embodiment, the activation tab 104 may be moved variably to allow for more or less liquid to permeate therethrough.

Figure 5:
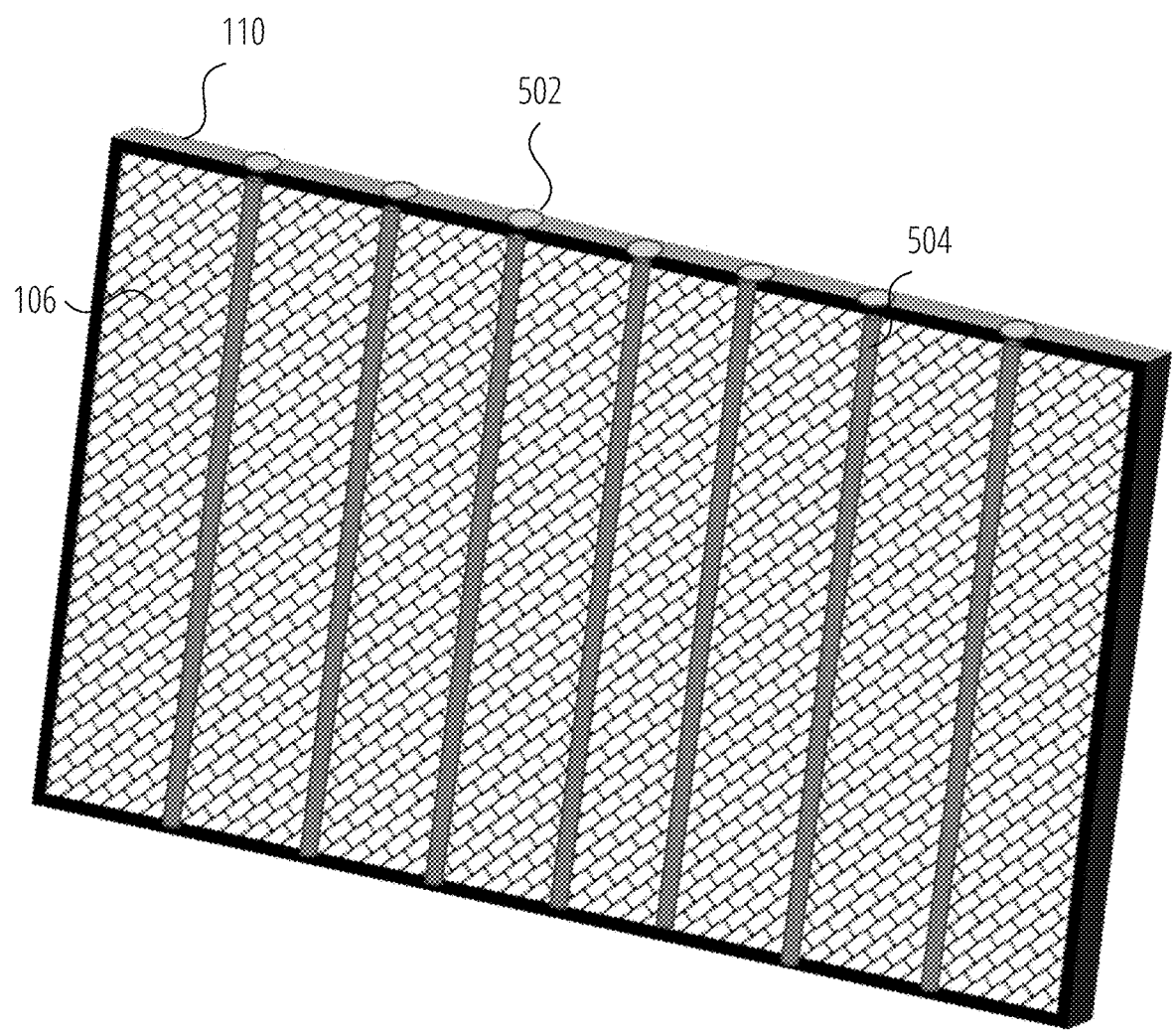
FIG. 5 illustrates a furnace filter with wicks in accordance with another embodiment.

FIG. 5 depicts another embodiment of the scented furnace filter 100. In this case the filter material 106 also includes one or more wick 504 to draw off the scented liquid 112 by capillary action and distribute the scented liquid 112 evenly across the filter material 106. The filter frame top section 110 is made of solid waterproof material, with permeable holes 502 at the top of each wick 504. When the scented liquid bar 102 is activated, the scented liquid 112 is dripping through these permeable holes 502 onto the wick 504.

Figure 6:
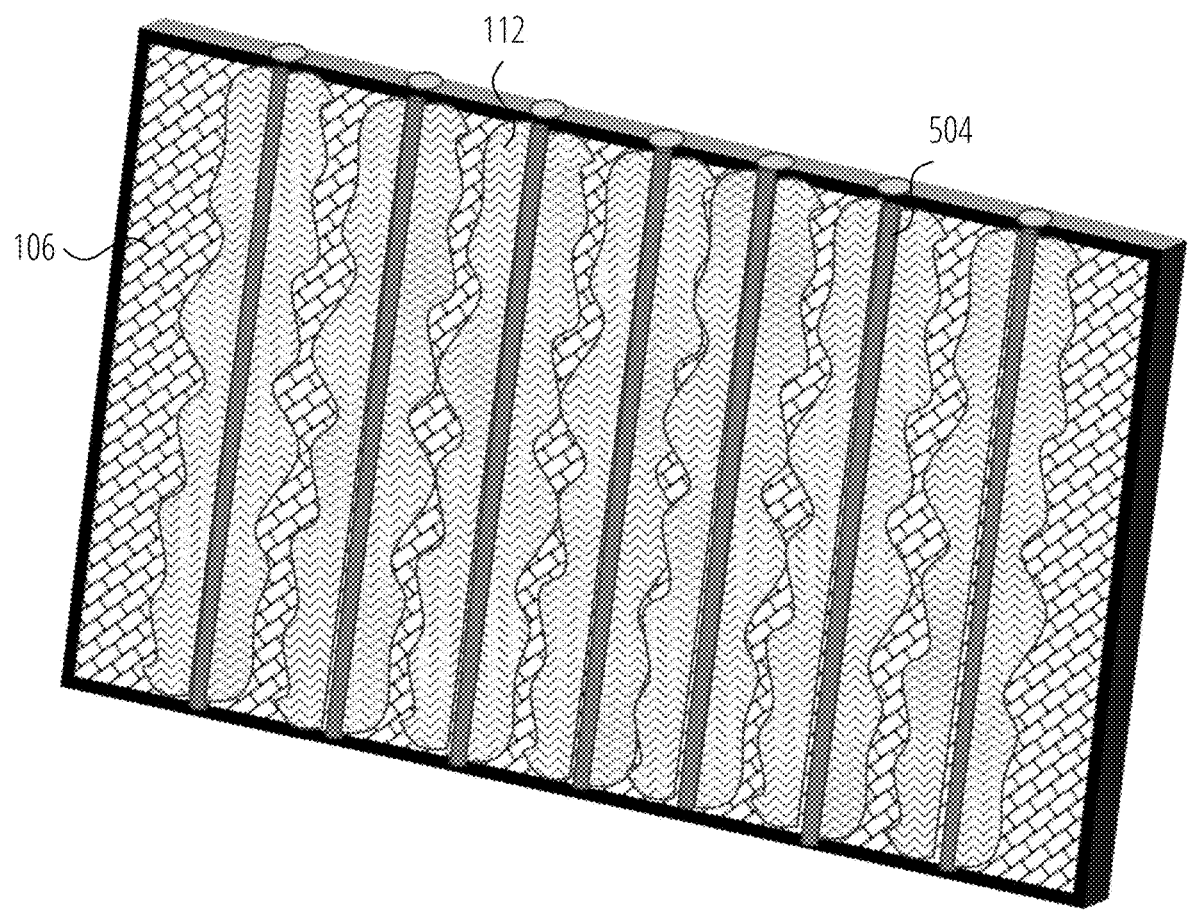
FIG. 6 illustrates an activated furnace filter with wicks in accordance with another embodiment.

FIG. 6 shows the scented liquid 112 being diffused from the wick 504 onto the filter material 106. With this embodiment, the scented liquid 112 is distributed evenly throughout the filter material 106 allowing for a more concentrated evaporation and scent distribution.

What is claimed is:

1. A scented furnace filter comprising:
   a filter frame installed in a furnace coupled with a filter material;
   said filter frame having a permeable filter frame top section;
   a scented liquid bar containing a scented liquid and having a permeable scented liquid bar base coupled to a removable activation tab;
   said scented liquid bar coupled to the permeable filter frame top section; and
   wherein when said removable activation tab is removed, said scented liquid permeates through said permeable scented liquid bar base and said permeable filter frame top section to soak said filter material such that air generated by the furnace going through the filter material evaporates the scented liquid to generate scented air to be distributed in a duct system to one or more supply register.

2. The scented furnace filter of claim 1 wherein said filter material comprises hemp.

3. The scented furnace filter of claim 1 further comprising one or more wickes distributed across the filter material to distribute the scented liquid evenly across the surface of the filter material.

4. The scented furnace filter of claim 1 wherein said removable activation tab is made of substantially flexible plastic.

5. The scented furnace filter of claim 1 wherein said scented liquid bar can be refilled with said scented liquid.

6. The scented furnace filter of claim 1 wherein said scented liquid bar can be replaced.

7. The scented furnace filter of claim 1 wherein said scented liquid is an essential oil.

8. The scented furnace filter of claim 1 wherein said scented liquid bar base comprises one or more permeable holes and said activation tab has holes at different locations such that in a closed position the activation tab acts as a waterproof barrier and when the removable activation tab is pulled outwardly it can modify an amount of said scented liquid that permeates to the filter material.

* * * * *